(12) United States Patent
Rutherford

(10) Patent No.: US 8,071,131 B2
(45) Date of Patent: Dec. 6, 2011

(54) MINERALIZING COMPOSITE MATERIALS FOR RESTORING TEETH

(75) Inventor: Bruce Rutherford, Seattle, WA (US)

(73) Assignee: Ivoclar Vivadent, Inc., Amherst, NY (US)

( * ) Notice: Subject to any disclaimer, the term of this patent is extended or adjusted under 35 U.S.C. 154(b) by 162 days.

(21) Appl. No.: 11/572,013

(22) PCT Filed: Jul. 11, 2005

(86) PCT No.: PCT/US2005/024409
§ 371 (c)(1),
(2), (4) Date: Aug. 1, 2007

(87) PCT Pub. No.: WO2006/019649
PCT Pub. Date: Feb. 23, 2006

(65) Prior Publication Data
US 2008/0108019 A1    May 8, 2008

Related U.S. Application Data

(60) Provisional application No. 60/589,214, filed on Jul. 15, 2004.

(51) Int. Cl.
*A61K 9/14* (2006.01)
*A61C 5/08* (2006.01)
*A61C 5/04* (2006.01)

(52) U.S. Cl. ........ 424/484; 424/486; 433/219; 433/226; 530/812; 530/815

(58) Field of Classification Search .......... 435/174, 435/176, 177, 178, 179, 180, 182; 530/811, 530/812, 813, 814, 815, 817; 424/484, 486; 514/2

See application file for complete search history.

(56) References Cited

U.S. PATENT DOCUMENTS

| | | | |
|---|---|---|---|
| 5,562,895 A | 10/1996 | Tung | |
| 5,866,629 A * | 2/1999 | Santerre et al. | 523/118 |
| 6,156,572 A * | 12/2000 | Bellamkonda et al. | 435/395 |
| 7,323,190 B2 * | 1/2008 | Chu et al. | 424/426 |
| 2002/0119424 A1 | 8/2002 | Margeas et al. | |
| 2003/0232071 A1 * | 12/2003 | Gower et al. | 424/443 |
| 2004/0002770 A1 | 1/2004 | King et al. | |
| 2004/0131562 A1 * | 7/2004 | Gower et al. | 424/57 |

FOREIGN PATENT DOCUMENTS

| | | |
|---|---|---|
| EP | 0 302 847 A2 | 2/1989 |
| GB | 1 509 977 A | 5/1978 |
| WO | 03/070290 A1 | 8/2003 |

OTHER PUBLICATIONS

Butler, "Dentin Matrix Proteins," Eur J Oral Sci 106(Supp 1):204-7 (1998).
Database WPI Week 200375, XP002529683, Thomson Scientific, London, GB; AN 2003-803741.
Huq et al., "Association of Bovine Dentine Phosphophoryn with Collagen Fragments," Archives of Oral Biology 50:807-19 (2005).
Supplemental European Search Report for European Patent Application No. EP05769534 (May 28, 2009).
International Search Report for PCT/US05/24409 (Jan. 6, 2006).
Written Opinion for PCT/US05/24409 (Jan. 6, 2006).

* cited by examiner

*Primary Examiner* — Jerry A Lorengo
*Assistant Examiner* — Noah Wiese
(74) *Attorney, Agent, or Firm* — Ann M. Knab

(57) ABSTRACT

Compositions and methods useful in restorative dentistry are disclosed. Compositions of the present invention include a peptide, and a polymer matrix. The peptide is one capable of reacting with a source of mineralizing ions to initiate deposition of hydroxyapatite crystals within the polymer matrix. Compositions of the present invention are uniquely capable of sealing a junction between a dental restorative material and adjacent native tooth tissue.

27 Claims, No Drawings

MINERALIZING COMPOSITE MATERIALS FOR RESTORING TEETH

This application claims the priority benefit of U.S. Provisional Patent Application Ser. No. 60/589,214, filed Jul. 15, 2004, which is hereby incorporated by reference in its entirety.

FIELD OF THE INVENTION

The present invention provides compositions and methods useful in the field of restorative dentistry.

BACKGROUND OF THE INVENTION

Tooth decay, or dental caries, initially results in the demineralization, and ultimately, in the complete destruction of tooth enamel and the underlying dentin. Currently, the restoration of carious teeth typically involves removing the demineralized enamel and dentin, followed by the placement of dental restoratives such as silver amalgams, cast gold inlays, ceramics, composite resins, and various organic polymers. However, despite major technological advances that have significantly improved the clinical performance of dental composite resins and ceramics, no current method of restoring teeth completely joins the alloplastic restorative material to the remaining mineralized natural tooth structure. Indeed, many dental restorations will ultimately fail because bacteria will penetrate this junction, leading to a condition known as recurrent caries.

Enamel is the hardest substance produced by a mammal's body. In mammals, the enamel layer of a tooth is formed during embryogenesis from protein secretions from ameloblast cells. As the tooth erupts, the layer of ameloblast cells is shed, and no more enamel can be naturally produced. Many groups have studied the formation of enamel and have attempted to imitate enamel formation and mineralization through various tissue engineering techniques.

There are two major groups of proteins found in the developing extracellular matrix ("ECM") of enamel: amelogenins and enamelins. The amelogenins constitute 90% of the ECM proteins and are lost during mineralization. Deutsch et al., *J. Biol. Chem.* 266:16021-16028 (1991). Conversely, the enamelins constitute only a minor fraction of the ECM proteins, but are partially retained in mature dental tissue. The acidic nature of enamelins (they include glutamic acid, aspartic acid, serine, and glycine residues), as well as their beta-pleated sheet structure, suggests a role in nucleation and regulation of enamel crystal growth. Recognizing this, U.S. Pat. No. 4,672,032 to Slavkin et al. provides methods for the formulation of dental enamel crystals in a biosynthetic matrix by the nucleation of calcium solutions with enamel proteins, and for the use of these enamel crystals as a dental restorative material. The methods assume the carious lesion does not extend into the tooth structure beyond the dentin/enamel junction ("DEJ"). In addition, the method does not provide for a rigid support capable of sustaining masticatory forces until the nascent enamel eventually becomes mineralized.

U.S. Pat. No. 5,071,958 to Hammarstrom et al. describes a process utilizing enamel matrix proteins for inducing binding between parts of living mineralized tissue by regeneration of mineralized tissue on at least one of the parts. Similar to Slavkin et al., however, the enamel matrix proteins are not applied within a rigid support, and are therefore unable to withstand masticatory crushing forces.

Recent advances in calcium phosphate chemistry have produced dental composite formulations that promise to remineralize demineralized enamel, dentin and cementum. See, U.S. Pat. No. 6,398,859 to Dickens et al., for example. These compounds are able to react with water to release calcium phosphate with release kinetics predicted to produce hydroxyapatite or fluoroapatite. However, the released mineral does not remain associated with the composite, but is instead deposited on the tooth surface. Currently, there is no known dental restorative material that has the ability to incorporate or form highly ordered mineral, such as hydroxyapatite or fluoroapatite, after placement, thereby sealing the junction between the restorative material and adjacent dental tissue.

The present invention is directed to overcoming these and other deficiencies in the art.

SUMMARY OF THE INVENTION

One aspect of the present invention relates to a mineralizing dental composite material useful in restorative dentistry. The material contains a peptide, and a polymer matrix. The peptide is one capable of reacting with a source of mineralizing ions to initiate deposition of hydroxyapatite crystals within the polymer matrix.

Another aspect of the present invention relates to a method of performing a direct dental restoration, which involves applying an effective restorative amount of a mineralizing dental composite material of the present invention, to a prepared area of native tooth tissue in need of restoration.

A further aspect of the present invention relates to a method of sealing a direct dental restoration to native tooth tissue. The method involves applying an effective luting and sealing amount of a mineralizing dental composite material of the present invention, to a junction between a direct dental restoration and adjacent native tooth tissue.

Yet another aspect of the present invention relates to a method of sealing an indirect dental restoration to native tooth tissue. The method involves applying an effective luting and sealing amount of a mineralizing dental composite material of the present invention, to a junction between an indirect dental restoration and adjacent native tooth tissue.

Still another aspect of the present invention relates to a method of sealing a dental restorative material to native tooth tissue. The method involves applying an effective luting and sealing amount of the mineralizing dental composite material of the present invention, to a junction between a dental restorative material and adjacent native tooth tissue.

Yet a further aspect of the present invention relates to a method of sealing a junction between a dental restorative material and native tooth tissue. The method involves applying an effective luting and sealing amount of a mineralizing dental composite material of the present invention, to the junction between a dental restorative material and adjacent native tooth tissue.

The present invention thus provides compositions and methods that are uniquely capable of sealing a junction between a dental restorative material and adjacent tooth tissue, such that the junction is essentially sealed to bacterial penetration.

DETAILED DESCRIPTION OF THE INVENTION

Formation and subsequent mineralization of dentin, the major hard tissue component of teeth, occurs through a process known as dentinogenesis. This process primarily involves the activity of odontoblasts, specialized secretory cells lining the dental pulp cavity. Mature odontoblasts synthesize and secrete a unique set of collagenous and non-collagenous proteins that give rise to a fibrillar nonmineralized extracellular matrix known as predentin, and that secrete dentin sialophosphoprotein ("DSPP"), which brings about the deposition of mineral in and around collagen bundles, forming dentin. The uncalcified predentin consists primarily of type I collagen fibrils. As predentin gradually transforms into dentin, the collagen fibrils become mineralized across a continuum beginning at the mineralization front (dentin), and extending toward the distal odontoblast layer. This highly regulated process generates plate-like hydroxyapatite ("HA") crystals, which are arranged primarily with their c-axis parallel to the collagen fibers.

In general, crystals form when the component ions of the crystal lattice come together with the right orientation, and with sufficient energy, to generate the first stable crystal or nucleus. Nucleation is followed by the addition of further ions or ion clusters to the nucleus as the crystal grows. Macromolecules within an organic matrix can facilitate the deposition of crystal by sequestering additional ions, effectively increasing the local ionic concentration, and creating a structure on which heterogeneous nucleation can occur.

The mineral content of dentin, as well as bone, is hydroxyapatite, which is closely associated with the extracellular collagen matrix. Collagen fibrils provide a framework for the deposition of crystals, both orienting the nascent crystal and providing a stable support for mineralized crystals and other matrix proteins. Although 90% of the organic matrix is collagen (Crit. Rev. Oral. Biol. Med. 64:541-547 (1993)), the ECM also contains non-collagenous proteins, which appear to regulate mineralization in both dentin and bone.

Recent advances in characterizing the major non-collagenous proteins of dentin have revealed the amino acid sequence of, among others, dentin sialophosphoprotein ("DSPP"), a precursor of dentin sialoprotein ("DSP") and dentin phosphoprotein ("DPP"). The amino acid sequence of DPP reveals numerous domains consisting of multiple highly charged aspartic acid and phosphoserine residues ("DS*S*") arranged linearly with long ridges of carboxylate and phosphate on a peptide backbone. The strong anionic character of DPP provides a high affinity for calcium ions, and when immobilized by binding to collagen fibrils, DPP functions as a hydroxyapatite nucleator in vivo.

Accordingly, one aspect of the present invention is a mineralizing dental composite material useful in restorative dentistry. The composite contains a peptide, and a polymer matrix. The peptide is one capable of reacting with a source of mineralizing ions to initiate deposition of hydroxyapatite crystals within the polymer matrix.

Preferably, the peptide contains a plurality of DS*S* (aspartic acid/phosphoserine/phosphoserin) domains. The peptide may, for example, be derived from dentin sialophosphoprotein, or dentin phosphoprotein.

The source of mineralizing ions will preferably provide calcium and phosphate ions. When the mineralizing dental composite material of the present invention is utilized in a direct dental restoration, for example, saliva can provide the source of calcium and phosphate ions. Mineralizing ions, such as, for example, calcium and phosphate ions, may also be provided with a calcium and phosphate-containing mouth wash or mouth rinse, for example. Alternatively, for example, the mineralizing dental composite material of the present invention may be present in combination with a calcium and phosphate-containing dental restorative material, such as, for example, a calcium phosphate dental resin or cement.

The polymer matrix may, for example, be a biosynthetic polymer matrix. The polymer matrix may, for example, be a collagen matrix. The collagen matrix may, for example, be produced in vitro, by cells, such as, for example, murine MC 3T3 preosteoblast clones. The polymer matrix may, for example, contain collagen peptides, or fragments of collagen peptides sufficient for properly organized hydroxyapatite crystal deposition to occur therein. The polymer matrix may, for example, be of any conventional dental resin polymer. The polymer matrix may, for example, be formed of enamel proteins, such as, for example, amelogenins, enamelins, or mixtures thereof. The polymer matrix may, for example, be formed of other biologically active peptides, such as, for example, fibronectin, tenascin, laminin, or chitin.

The mineralizing dental composite material of the present invention is useful in restorative dentistry. The mineralizing dental composite material is useful, for example, as a direct tooth filling material, in a method of performing a direct tooth restoration. The material may be used alone, or in combination with, for example, a calcium phosphate dental resin or cement.

The mineralizing dental composite material of the present invention is further useful as a dental cement-like material, such as, for example, in methods of sealing direct or indirect dental restorations, or other dental restorative materials, to native tooth tissue. Other dental restorative materials may include, for example, such materials as dental bases or liners.

In addition to adhering conventional dental restorative materials to native tooth tissue, the mineralizing dental composite material of the present invention may be used, for example, to adhere fabricated natural tooth tissue to native dental tissue. Fabricated natural tooth tissue may include, for example, enamel, dentin, or compound structures containing enamel, dentin, and a dentin/enamel junction ("DEJ"), produced ex vivo or in vitro.

Unlike prior art dental restorative materials and cements, the mineralizing dental composite material of the present invention is uniquely capable of sealing the junction between the dental restorative material and the native tooth tissue. Unlike other restorative materials, which are asserted to produce and deposit hydroxyapatite or fluorapatite on the tooth surface, the mineralizing dental composite material of the present invention provides a similarly mineralized matrix contiguous with the native tooth tissue, effectively sealing the junction against infiltration by bacteria.

Although preferred embodiments have been depicted and described in detail herein, it will be apparent to those skilled in the relevant art that various modifications, additions, substitutions, and the like can be made without departing from the spirit of the invention and these are therefore considered to be within the scope of the invention as defined in the claims which follow.

What is claimed:

1. A mineralizing dental composite material useful in restorative dentistry, comprising:
    a peptide comprising a plurality of aspartic acid/phosphoserine/phosphoserine (DS*S*) domains; and
    a polymer matrix;
    wherein said peptide is capable of reacting with a source of mineralizing ions to initiate deposition of hydroxyapatite crystals within said polymer matrix; and
    wherein said polymer matrix comprises dental resin polymers.

2. The mineralizing dental composite material of claim 1, wherein said peptide is derived from dentin sialophosphoprotein, or dentin phosphoprotein.

3. The mineralizing dental composite material of claim 1, wherein said mineralizing ions comprise calcium and phosphate ions.

4. The mineralizing dental composite material of claim 3, wherein said source of calcium and phosphate ions is saliva.

5. The mineralizing dental composite material of claim 1, further comprising a calcium and phosphate-containing dental restorative material.

6. The mineralizing dental composite material of claim 5, wherein said calcium and phosphate-containing dental restorative material comprises a calcium phosphate dental resin or cement.

7. The mineralizing dental composite material of claim 1, wherein said polymer matrix comprises collagen.

8. The mineralizing dental composite material of claim 1, wherein said polymer matrix comprises collagen peptides.

9. The mineralizing dental composite material of claim 1, wherein said polymer matrix comprises collagen peptide fragments.

10. The mineralizing dental composite material of claim 1, wherein said polymer matrix comprises one or more enamel proteins.

11. The mineralizing dental composite material of claim 10, wherein said polymer matrix comprises one or more amelogenins, enamelins, or a mixture thereof.

12. The mineralizing dental composite material of claim 1, wherein said polymer matrix comprises biologically active peptides selected from the group consisting of fibronectin, tenascin, laminin, and chitin.

13. A method of performing a direct dental restoration, comprising:
    applying an effective restorative amount of the mineralizing dental composite material of claim 1, to a prepared area of native tooth tissue in need of restoration.

14. A method of performing a direct dental restoration, comprising:
    applying an effective restorative amount of the mineralizing dental composite material of claim 2, to a prepared area of native tooth tissue in need of restoration.

15. A method of performing a direct dental restoration, comprising:
    applying an effective restorative amount of the mineralizing dental composite material of claim 6, to a prepared area of native tooth tissue in need of restoration.

16. A method of sealing a direct dental restoration to native tooth tissue, comprising:
    applying an effective luting and sealing amount of the mineralizing dental composite material of claim 1, to a junction between a direct dental restoration and adjacent native tooth tissue.

17. A method of sealing a direct dental restoration to native tooth tissue, comprising:
    applying an effective luting and sealing amount of the mineralizing dental composite material of claim 2, to a junction between a direct dental restoration and adjacent native tooth tissue.

18. A method of sealing a direct dental restoration to native tooth tissue, comprising:
    applying an effective luting and sealing amount of the mineralizing dental composite material of claim 6, to a junction between a direct dental restoration and adjacent native tooth tissue.

19. A method of sealing an indirect dental restoration to native tooth tissue, comprising:
    applying an effective luting and sealing amount of the mineralizing dental composite material of claim 1, to a junction between an indirect dental restoration and adjacent native tooth tissue.

20. A method of sealing an indirect dental restoration to native tooth tissue, comprising:
    applying an effective luting and sealing amount of the mineralizing dental composite material of claim 2, to a junction between an indirect dental restoration and adjacent native tooth tissue.

21. A method of sealing an indirect dental restoration to native tooth tissue, comprising:
    applying an effective luting and sealing amount of the mineralizing dental composite material of claim 6, to a junction between an indirect dental restoration and adjacent native tooth tissue.

22. A method of sealing a dental restorative material to native tooth tissue, comprising:
    applying an effective luting and sealing amount of the mineralizing dental composite material of claim 1, to a junction between a dental restorative material and adjacent native tooth tissue.

23. A method of sealing a dental restorative material to native tooth tissue, comprising:
    applying an effective luting and sealing amount of the mineralizing dental composite material of claim 2, to a junction between a dental restorative material and adjacent native tooth tissue.

24. A method of sealing a dental restorative material to native tooth tissue, comprising:
    applying an effective luting and sealing amount of the mineralizing dental composite material of claim 6, to a junction between a dental restorative material and adjacent native tooth tissue.

25. A method of sealing a junction between a dental restorative material and native tooth tissue, comprising:
    applying an effective luting and sealing amount of the mineralizing dental composite material of claim 1, to a junction between a dental restorative material and adjacent native tooth tissue.

26. A method of sealing a junction between a dental restorative material and native tooth tissue, comprising:
    applying an effective luting and sealing amount of the mineralizing dental composite material of claim 2, to a junction between a dental restorative material and adjacent native tooth tissue.

27. A method of sealing a junction between a dental restorative material and native tooth tissue, comprising:
    applying an effective luting and sealing amount of the mineralizing dental composite material of claim 6, to a junction between a dental restorative material and adjacent native tooth tissue.

* * * * *